United States Patent [19]
Webb

[11] Patent Number: 6,059,794
[45] Date of Patent: May 9, 2000

[54] UMBILICAL CORD BLOOD EXTRACTOR

[75] Inventor: Nicholas J. Webb, Wrightwood, Calif.

[73] Assignee: Cetus, L.C., San Antonio, Tex.

[21] Appl. No.: 09/067,510

[22] Filed: Apr. 27, 1998

Related U.S. Application Data

[63] Continuation-in-part of application No. 08/840,746, Apr. 16, 1997, Pat. No. 5,860,989.

[51] Int. Cl.$^7$ ............................................ A61B 17/42
[52] U.S. Cl. ................................. 606/120; 604/4
[58] Field of Search ........................... 606/120; 604/4; D7/665, 666

[56] References Cited

U.S. PATENT DOCUMENTS

| | | | |
|---|---|---|---|
| D. 390,068 | 2/1998 | Schulze | D7/666 |
| 5,190,556 | 3/1993 | Hessel | 606/120 |
| 5,342,328 | 8/1994 | Grossman | 604/317 |
| 5,372,581 | 12/1994 | Anderson | 604/32 |
| 5,415,665 | 5/1995 | Hessel | 606/120 |
| 5,520,699 | 5/1996 | Hessel | 606/120 |
| 5,575,795 | 11/1996 | Anderson | 606/120 |
| 5,797,922 | 8/1998 | Hessel et al. | 606/120 |

*Primary Examiner*—Gary Jackson
*Assistant Examiner*—Julian W. Woo
*Attorney, Agent, or Firm*—David P. Gordon; David S. Jacobson; Thomas A. Gallagher

[57] ABSTRACT

An umbilical cord blood extractor includes a lower tray for receiving the cord and an upper lid for squeezing the cord. The lower tray and upper lid are preferably couplable at one end at pivot locations or a hinge. The lower tray is provided with a longitudinal trough and a distal blood reservoir for collecting blood. The trough is closed at its proximal end and opens into the reservoir at its distal end. A blood collection needle is preferably provided in the lower tray at a lower portion of the reservoir. The upper lid is formed with a preferably proximally to distally tapered, longitudinal protrusion (plunger) sized such that when the upper lid is rotated toward the lower tray, on the pivots or at the hinge, the plunger enters into the trough and squeezes a section of umbilical cord located therein.

21 Claims, 10 Drawing Sheets

UMBILICAL CORD BLOOD EXTRACTOR

This application is a continuation-in-part of U.S. Ser. No. 08/840,746, filed on Apr. 16, 1997, which is hereby incorporated by reference herein in its entirety and is now U.S. Pat. No. 5,860,989.

BACKGROUND OF THE INVENTION

1. Field of the Invention

This invention relates broadly to medical instruments. More particularly, this invention relates to an umbilical cord blood extractor which extracts placental blood from a cut section of umbilical cord.

2. State of the Art

The umbilical cord serves as the conduit between a mother and a fetus developing in the womb of the mother. Nutrients and oxygen within the blood of the mother pass through the umbilical cord to the fetus. Immediately after a baby is born, the umbilical cord is clamped to stop the flow of blood through the umbilical cord. The umbilical cord is then cut to free the baby from the placenta.

In accord with standard medical procedure, after birth, the blood from the umbilical cord is sampled, and chemical and biological assays are performed on the blood. The assays are used to determine whether a potential mismatch exists between mother and baby blood types and whether the baby is subject to potential genetically transmitted diseases, bacterial diseases, and viral infections, such as human immunodeficiency viruses which lead to AIDS and hepatitis B and C. Generally, it is desirable to recover the cord blood sample quickly and safely given the time and health concerns of the practitioner within managed health care systems.

A quick method of sampling blood from the cord is to manually milk blood from the section of cut cord; i.e., to squeeze the section of cut umbilical cord by hand to rapidly and thoroughly remove blood from the cord. However, this is not usually practical. The umbilical cord is coated with various fluids, e.g., vaginal blood, amniotic fluid and Wharton's gel, making the cord slippery and hard to handle. Furthermore, it is desirable to minimize contact between health care workers and such fluids. In fact, federal law and an association of operating room nurses have mandated protecting health care workers from blood born pathogens.

A number of devices have been disclosed for taking a sample of blood from an umbilical cord which do not require manually milking the cord. U.S. Pat. No. 5,575,795 to Anderson discloses an umbilical cord holder having an elongate portion with a curved open trough and clamps at either end of the elongate portion. A health care worker places the umbilical cord into the trough and seals the ends of the umbilical cord with the clamps. While holding the elongate portion, the practitioner inserts a needle through the open trough and into the cord and a syringe is operated to withdraw blood from the cord. However, this device has several drawbacks. First, the device requires the use of two hands to extract blood, one to hold the elongate portion and one to operate the needle and syringe. Second, the device requires the use of a needle which must be inserted through the open trough and into the cord. As a result, there exists the potential for unintentional needle pricking, and exposure to blood borne pathogens such as HIV and hepatitis. Third, the blood collected in the syringe must then be transferred from the syringe to one or more vials, which creates an additional risk of unintentional pricking. Fourth, the procedure to extract blood from the cord using this device is substantially time consuming.

U.S. Pat. No. 5,415,665 to Hessel et al. discloses a device which clamps, cuts, and extracts blood from an umbilical cord. The device includes a clamshell housing provided with a removable cord clamp, a cutting apparatus, and valved blood collection vials. However, the Hessel et al. device does not provide a safe method for removing blood. The device must be hand held while cutting the cord and during the collection the blood. Therefore, during cord cutting and blood collection the likelihood of contact between the practitioner and blood is not minimized. In addition, the device is relatively complex and, seemingly relatively difficult to manufacture.

U.S. Pat. No. 5,342,328 to Grossman et al. discloses an alternative to Hessel. The device is a cup having a lower blood reservoir. A cut section of umbilical cord is placed into the cup and allowed to gravity drain into the reservoir. Once the blood has drained, the blood is then transferred to a vial. Very little handling of the cut cord is required once the cord is in the cup. However, the design of the Grossman et al patent requires the gathering of a large section of umbilical cord, as blood is not squeezed from the cord member as in the manual method, or directly extracted by needle and syringe as in Anderson. In addition, the system requires waiting for the blood to drain into the blood reservoir, making it highly impractical given the time concerns mandated by managed health care.

SUMMARY OF THE INVENTION

It is therefore an object of the invention to provide an apparatus for rapidly extracting blood from an umbilical cord.

It is another object of the invention to provide an apparatus which minimizes contact between a practitioner and blood being extracted from an umbilical cord.

It is a further object of the invention to provide an apparatus which is inexpensive and easy to manufacture and which extracts blood from an umbilical cord.

In accord with these objects which will be discussed in detail below, an umbilical cord blood extractor is provided and broadly comprises means for receiving the cord, means for squeezing the cord, and preferably means for collecting the blood from the cord. In preferred embodiments, the umbilical cord blood extractor includes a lower tray for receiving the cord and an upper lid for squeezing the cord. The lower tray and upper lid are preferably coupled at a hinge or couplable at a pivot location. The lower tray is provided with a longitudinal trough and a distal blood reservoir for collecting blood. The trough is closed at its proximal end and opens into the reservoir at its distal end. A blood collection needle is preferably provided in the lower tray at a lower portion of the reservoir. The upper lid is formed with a longitudinal protrusion (plunger) sized such that when the upper lid is rotated toward the lower tray, at the hinge or the pivot, the plunger enters into the trough.

It will be appreciated that blood from a cut section of umbilical cord may be quickly sampled using the umbilical cord blood extractor of the invention. For purposes herein, a 'cut section' of umbilical cord means both a section of umbilical cord severed at both of its end such that it is no longer attached to the placenta or the child, and also a section of umbilical cord which remains attached at one of its ends to the placenta or the child, but which has been severed at its other end from the other of the placenta and the child. With the upper lid of the blood extractor in an open position, the cut section of umbilical cord is placed into the trough of the lower tray such that a severed end of the cut section is directed toward the reservoir. The upper lid is then rotated about the lower tray (at the hinge or pivot) such that the plunger aligns with the trough and places pressure along the cord. Because the upper lid is rotated, the plunger squeezes the cord starting near the proximal end of the trough and proceeds to apply squeezing pressure toward the distal end. The blood is thereby 'milked' into the reservoir. Once a sufficient amount of blood has been collected in the reservoir, the blood can be withdrawn by coupling an evacuated vial to the blood collection needle.

Other embodiments of the invention are also provided. In one embodiment a movable member which includes a cylindrical squeezing member is utilized instead of a plunger in order to squeeze the umbilical cord.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 2:
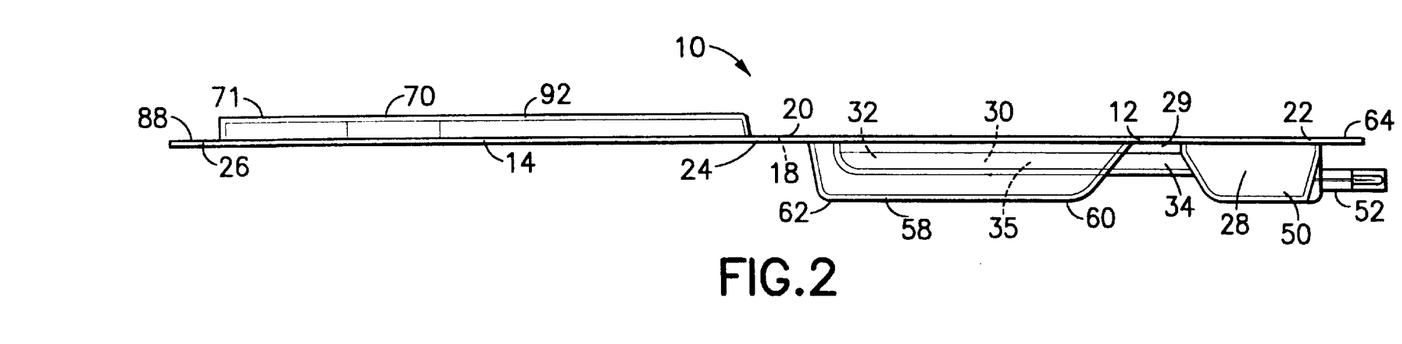
FIG. 2 is a side elevation view of the umbilical cord blood extractor in an open position according to the first embodiment of the invention.
Figure 3:
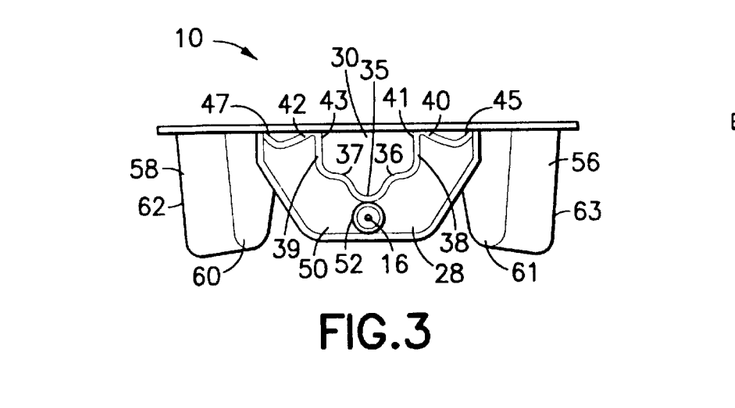
FIG. 3 is a transparent front end view of the lower tray of the umbilical cord blood extractor of FIGS. 1 and 2 in an open position.
Figure 4:
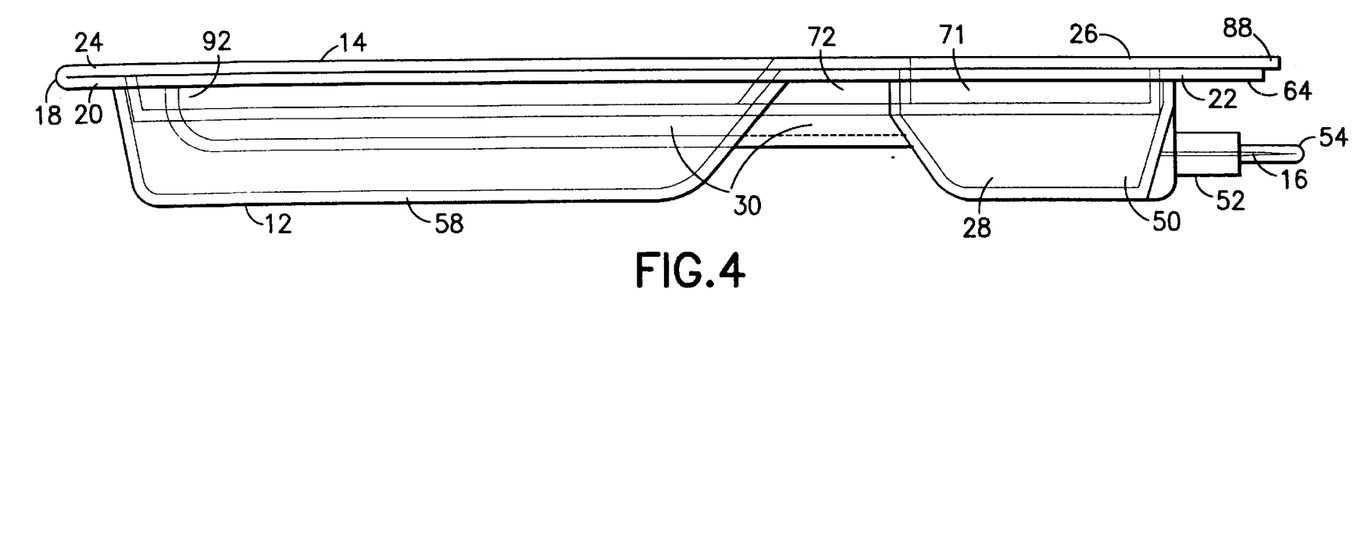
FIG. 4 is a transparent side elevation view of the umbilical cord blood extractor of FIGS. 1 through 3 in a closed position.
Figure 5:
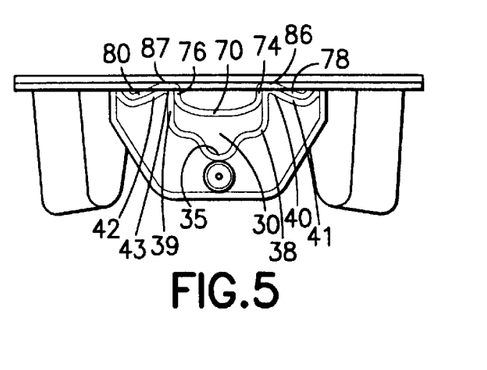
FIG. 5 is a transparent front end view of the umbilical cord blood extractor of FIGS. 1 through 3 in a closed position.

Turning now to FIGS. 1 through 5, an umbilical cord blood extractor 10 according to a first embodiment of the invention is shown. Generally, the blood extractor includes a lower tray 12, an upper lid 14, and a blood collection needle 16. The lower tray 12 and upper lid 14 are connected by a live hinge 18, enabling the upper lid 14 to rotate along the hinge 18 from an open position (FIGS. 1 and 2) upward and over toward the lower tray 12 and to interlock with the lower tray in a closed position (as shown in FIGS. 4 and 5). The lower tray 12 has a proximal end (hinged end) 20 and a distal end (free end) 22 and the upper lid has a proximal end (hinged end) 24 and distal end (free end) 26.

Figure 1:
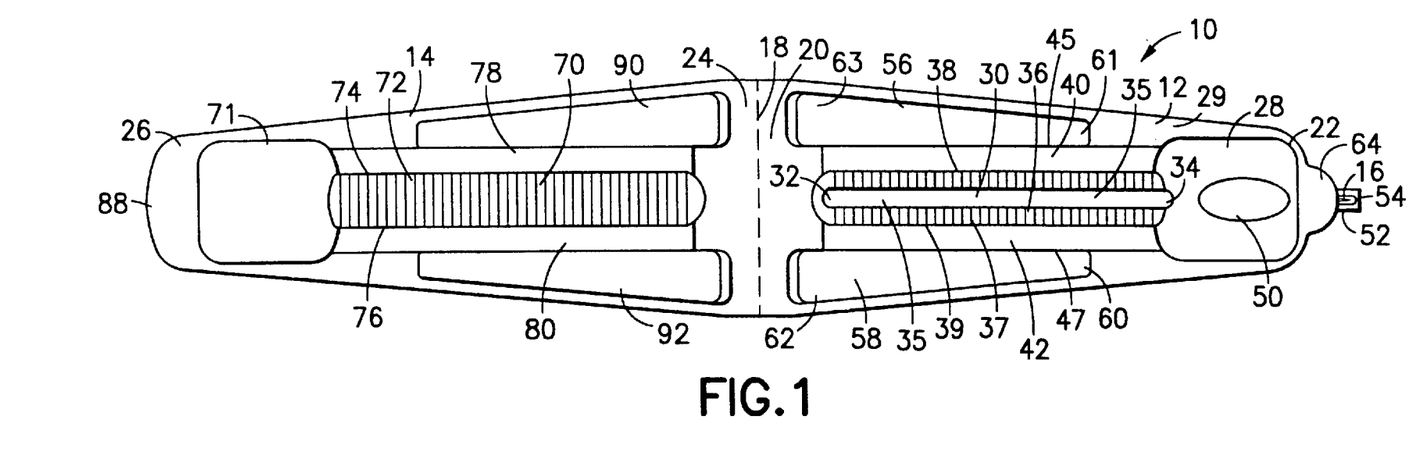
FIG. 1 is a top view of an umbilical cord blood extractor in an open position according to a first embodiment of the invention.

Referring more particularly to FIGS. 1 through 3, the lower tray 12 is provided with an upper surface 29, a longitudinal trough 30 for receiving a cut section of umbilical cord, and a distal blood reservoir 28 for receiving and pooling blood. The trough 30 is closed at its proximal end 32 and opens into the reservoir 28 at its distal end 34. The trough 30 includes a recessed channel 35, lateral sloping sides 36, 37, and tray walls 38, 39. The recessed channel 35 preferably has a smooth surface and directs the flow of blood toward the blood reservoir 28. The lateral sloping sides 36, 37 are preferably serrated (i.e., they have transverse ribs). The tray walls 38, 39 are preferably substantially vertical and laterally confine a section of umbilical cord within the trough 30. Preferably concave tray surfaces 40, 42 are provided and slope laterally downward on either side of the tray walls 38, 39 and upward to lateral walls 45, 47. The tray walls 38, 39 and the tray surfaces 40, 42 are angled at acute angles relative to each other and intersect at intersections 41, 43. The tray surfaces 40, 42 are designed to capture, confine, and direct any fluid from a cut section of cord which is outside of the trough toward the blood reservoir 28.

The blood reservoir 28 preferably includes a well 50, located centrally but distally in the reservoir, which pools the blood and directs its flow into the blood collection needle 16. The blood collection needle 16 is provided in the lower tray 12 along a distal surface of the reservoir 28 adjacent the well 50. Preferably, the blood collection needle 16 is provided with a substantially rigid needle hub 52, and a tubular cap 54 to prevent unintentional skin pricking by the needle. The cap 54 may be rigid, or may be a protective flexible phlebotomy type boot, if desired.

Longitudinal legs 56, 58 are preferably provided lateral of the trough 30, and descend below the recessed channel 35 of the trough 30. The legs 56, 58 are preferably hollow, having an open top, and preferably taper in height, being shorter distally (at 60 and 61 in FIG. 2) and taller proximally (at 62 and 63 in FIG. 2). The legs also preferably taper in width for stability, being wider proximally (at 62 and 63) and narrower distally (at 60 and 61). At the distal end 22 of the lower tray and along the upper surface 29, a tray tab 64 is provided, the function of which is discussed in more detail below.

Referring to FIGS. 1, 2, 4, and 5, the upper lid 14 will now be described. For purposes of clarity, wherever directional orientation (e.g., 'up' and 'down', 'upper' and 'lower', etc.) or positional orientation is used in the description, the upper lid is being described with reference to a 'closed position', i.e., seated over the tray (generally as shown in FIGS. 4 and 5). The upper lid 14 is generally provided with a longitudinal protrusion or plunger 70 and a reservoir cap 71. The longitudinal plunger 70 includes a lower surface 72 and substantially vertical lid walls 74, 76 on either side of the lower surface 72. The lower surface 72 is preferably serrated and is also preferably slightly convex. The width of the plunger is such that when the upper lid 14 is in the closed position, the lid walls 74, 76 of the plunger 70 fit snugly inside the walls 38, 39 of the trough 30. Lid surfaces 78, 80 are provided which slope laterally downward on either side of the lid walls 74, 76 and seat over tray surfaces 40, 42 of the tray 12. The lid walls 74, 76 and the lid surfaces 78, 80 preferably meet at acutely angled lid intersections 86, 87 which are designed to seat over the tray intersections 41, 43.

The reservoir cap 71 is dimensioned to seat into the upper opening of the reservoir 28 to substantially seal the reservoir 28 and prevent blood pooled in the reservoir from escaping therefrom. At the distal end 22 of the upper lid 14, a lid tab 88 is provided. Lateral of the lid surfaces 78, 80, the lid 14 forms shallow leg caps 90, 92. The leg caps 90, 92 have substantially the same width and length as the legs and are designed for seating and locking by friction fit into an upper portion of the hollow legs 58, 60 of the lower tray 12.

Figure 6:
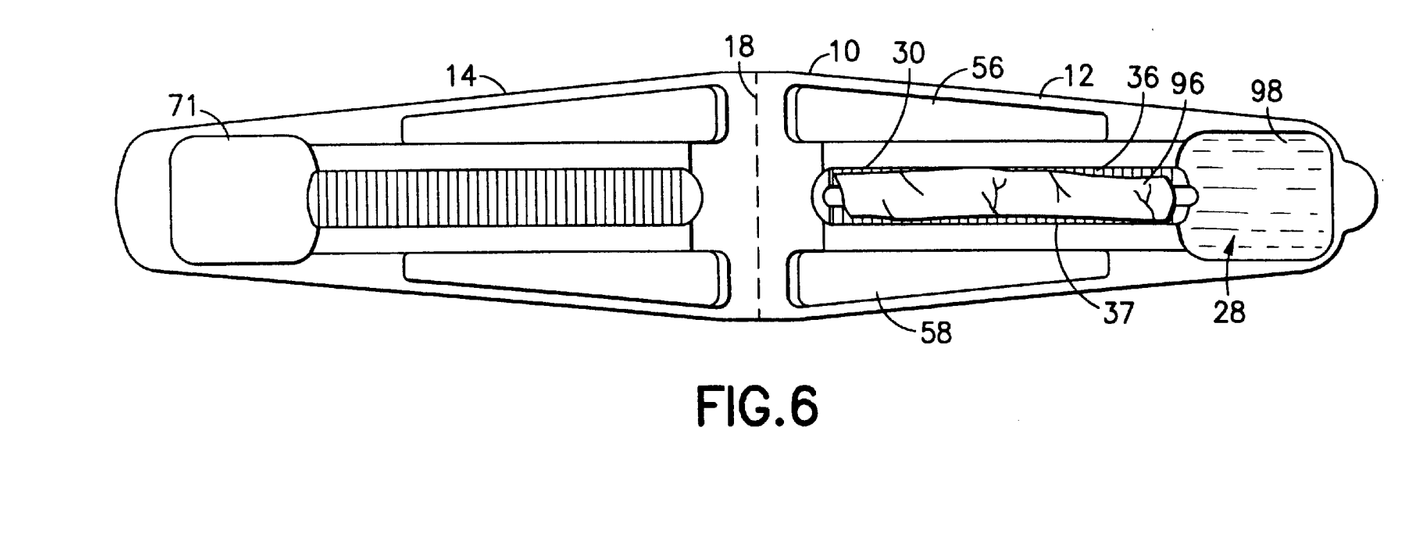
FIGS. 6 through 8 illustrate the method of the invention for extracting blood from a cut section of umbilical cord using the first embodiment of the umbilical cord extractor.
Figure 7:
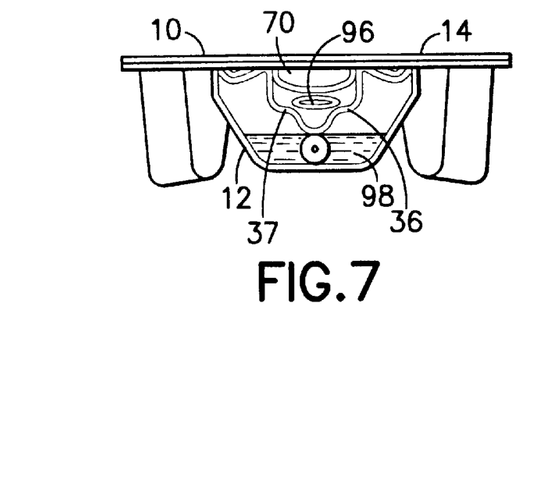
Figure 8:
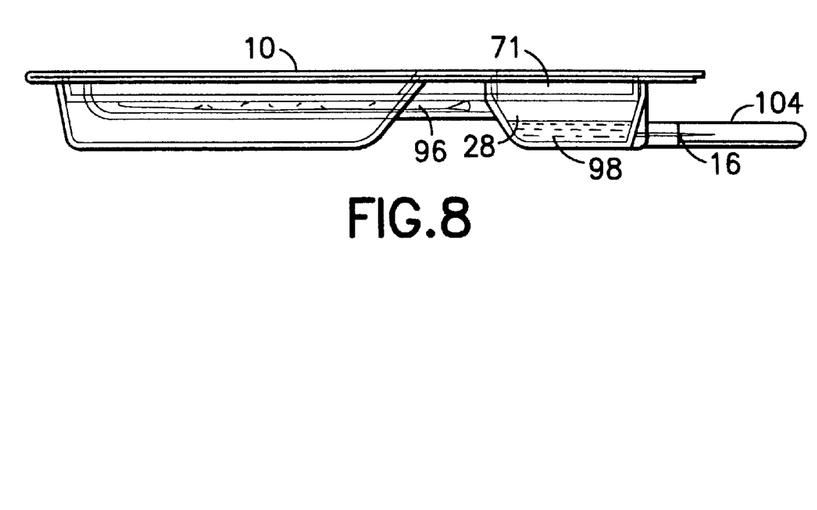
Figure 9:
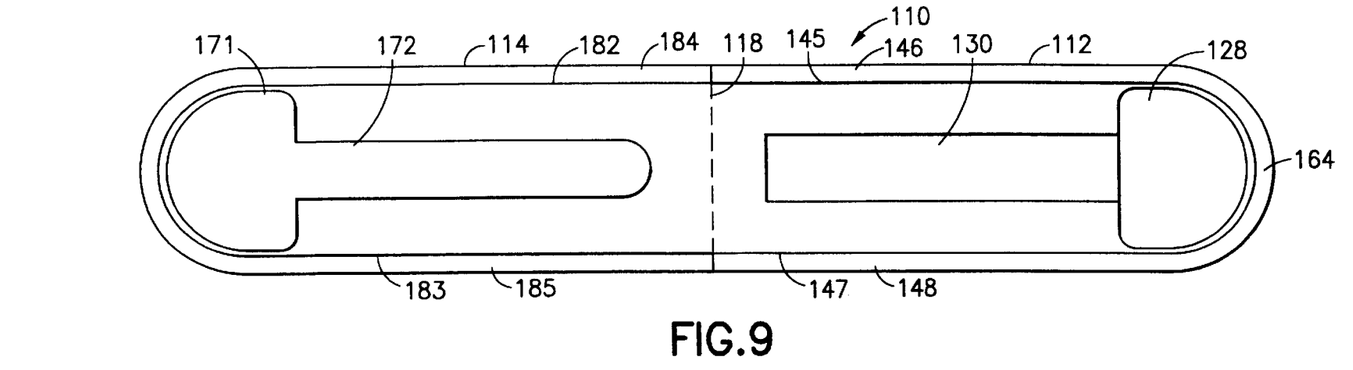
FIG. 9 is a top view of an umbilical cord blood extractor according to a second embodiment of the invention in an open position.

Turning to FIGS. 6 through 8, the use of the blood extractor is described. With particular reference to FIG. 6, a cut section of umbilical cord 96 is placed in the trough 30 of the lower tray 12 of the blood extractor 10. The cord is ideally positioned to rest upon the serrated surface of the lateral sloping sides 36, 37 of the trough. Referring to FIGS. 6 and 7, the upper lid 14 is next rotated about the hinge 18 to overlie the lower tray 12 and to cause the plunger 70 to enter the trough and squeeze the cord, thereby milking the cord blood 98 into the reservoir 28. The cord is preferably progressively squeezed by the plunger, squeezing the cord from its proximal end to its distal end. The serrations on both the sloping sides 36, 37 of the trough and on the lower surface of the plunger bite into the cord and prevent the cord from migrating distally as the extractor is closed.

Referring to FIGS. 1, 6, and 8, the reservoir cap 71 locks into the opening of the reservoir 28 and the leg caps 90, 92 lock into the opening at the upper portion of the legs 56, 58 to lock the upper lid 14 to the lower tray 12. In addition, the lid surfaces 78, 80 and lid intersections 86, 87 seat against the tray surfaces 40, 42 and tray intersections 41, 43 and prevent blood from splashing toward a practitioner as the blood collector is operated. When the blood extractor is placed on a horizontal surface, the tapered legs 56, 58 seat the blood collector at a downward angle (distal end lower than the proximal end) and enable blood to drain into the reservoir 28. If it becomes necessary to open the blood collector after the upper lid and lower tray are locked together, the tray tab 64 and lid tab 88 can be used to pull apart the upper lid from the lower tray.

Turning to FIG. 8, blood 98 is milked and drained from the cord 96 into the reservoir 28 until blood fills the well 50 of the reservoir, preferably to a level above the blood extraction needle 16. Once sufficient blood 98 is in the well 50, which can occur relatively quickly due to the milking action of the blood collector, the protective cover 54 (see FIG. 2) may be removed from the needle, if necessary, and an evacuated specimen vial 104 is coupled to the needle 16. Blood flows through the needle and into the vial. The specimen vial is removed, and, if desired, other specimen vials may be coupled to the needle to receive remaining blood in the reservoir. After the desired blood has been removed from the blood extractor 10, the blood extractor 10 and section of umbilical cord 96 may be discarded. It will be appreciated that the blood extractor provides a quick and safe means for extracting blood from the umbilical cord.

By way of example, and not by way of any limitation, the following dimensions are provided for the umbilical cord blood extractor 10. The length of the blood extractor in the open position is approximately 15.9 inches, and in a closed position is approximately 8 inches. The width of the blood extractor at the widest point is approximately 2.9 inches. The height of the blood extractor at its proximal end is approximately 1.0 inches and the height at its distal end is approximately 0.8 inches. The trough 30 is approximately 3.9 inches in length and has a width of approximately 0.9 inches. The reservoir 28 has an upper opening of approximately 1.9 inches in length, a lower surface of approximately 1.2 inches in length, and a substantially constant width of approximately 1.5 inches. The tapered legs 58, 60 are approximately 1.0 inches in height at their proximal end and 0.9 inches in height at their distal end. The leg caps 90, 92 and reservoir cap 71 extend approximately 0.2 inches from the surface of the upper lid 14.

The blood extractor 10 of the invention has been ideally designed for vacuum forming. As a result, the blood extractor 10 is preferably vacuum formed from a unitary piece of medical grade plastic, such as PETG. Vacuum forming permits the device to be made relatively inexpensively. The device may also be manufactured by way of injection molding, or by any other suitable manufacturing technique.

Turning now to FIGS. 9 through 12, a second embodiment of an umbilical cord blood extractor 110, substantially similar to the blood extractor 10 of the first embodiment (with like parts having numbers incremented by 100), is shown. The blood extractor 110 generally includes a lower tray 112, an upper lid 114, and a hinge 118 coupling the upper lid 114 to the lower tray 112. The lower tray 112 is provided with a longitudinal trough 130 which preferably tapers from its distal end to its proximal end. A blood reservoir 128 is provided at the distal end of the trough 130 for collecting blood. Raised walls 145, 147, each preferably having a laterally extending upper lip 146, 148, are provided along the lateral sides of the lower tray.

The upper lid 114 includes a longitudinal protrusion or plunger 172 which preferably tapers from its distal end to its proximal end. A reservoir cap 171 is provided at the distal end of the plunger 172 for seating in and frictionally engaging the upper opening of the reservoir 128. Descending walls 182, 183, each preferably having a laterally extending lower lip 184, 185, are provided along the lateral sides of the upper lid. The descending walls 182, 183 and lower lips 184, 185 of the upper lid 114 are designed to seat against the raised walls 145, 147 and upper lips 146, 148 of the lower tray 112.

Figure 10:
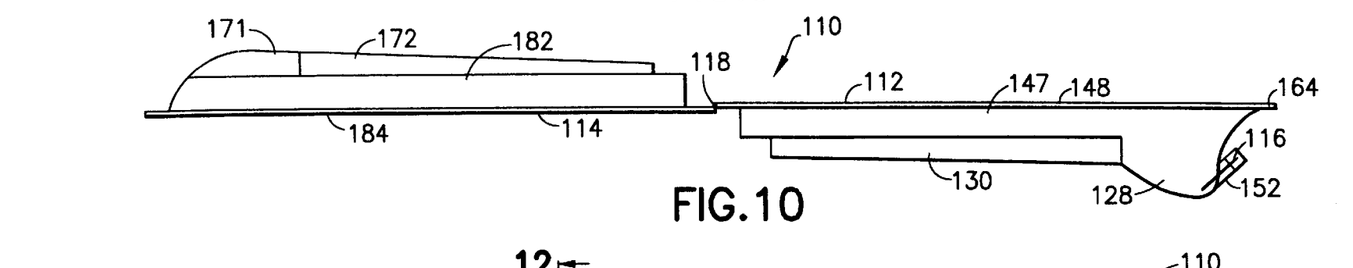
FIG. 10 is a side elevation view of the umbilical cord blood collector according to the second embodiment of the invention in an open position.
Figure 11:
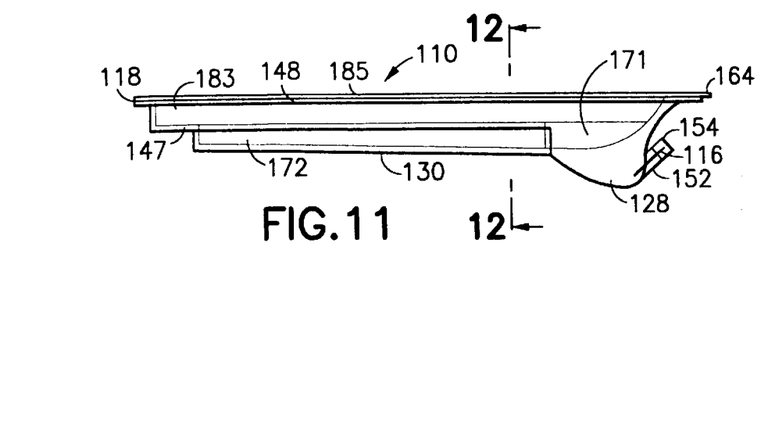
FIG. 11 is a transparent side elevation view of the umbilical cord blood collector according to the second embodiment of the invention in a closed position.
Figure 12:
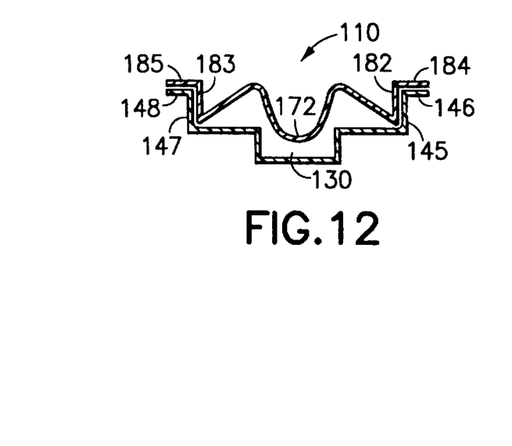
FIG. 12 is cross-section through line 12—12 in FIG. 11.

A needle hub 152 and needle 116 are provided in the lower tray at the reservoir 128 for coupling an evacuated vial for drawing blood collected in the reservoir. As shown in FIGS. 10 and 11, the needle 116 is shielded by a cap 154. In addition, the needle is preferably angled upward and is substantially shielded by tab 164.

In practice, a section of umbilical cord is placed into the tapered trough 130 of the lower tray 112 and the upper lid 114 is rotated onto the lower tray. The tapered plunger 172 of the upper lid enters into the trough to squeeze the cord and extract blood which drains into the reservoir 128 in the lower tray. The plunger preferably squeezes the proximal end of the cord first and progressively squeezes more distally. The tapered design of both the trough and plunger minimize the migration of the cord section within the trough. The set of walls 145, 147, 182, 183 and lips 146, 148, 184, 185 prevent blood from splashing onto a practitioner using the device.

Figures 13, 14, 15:
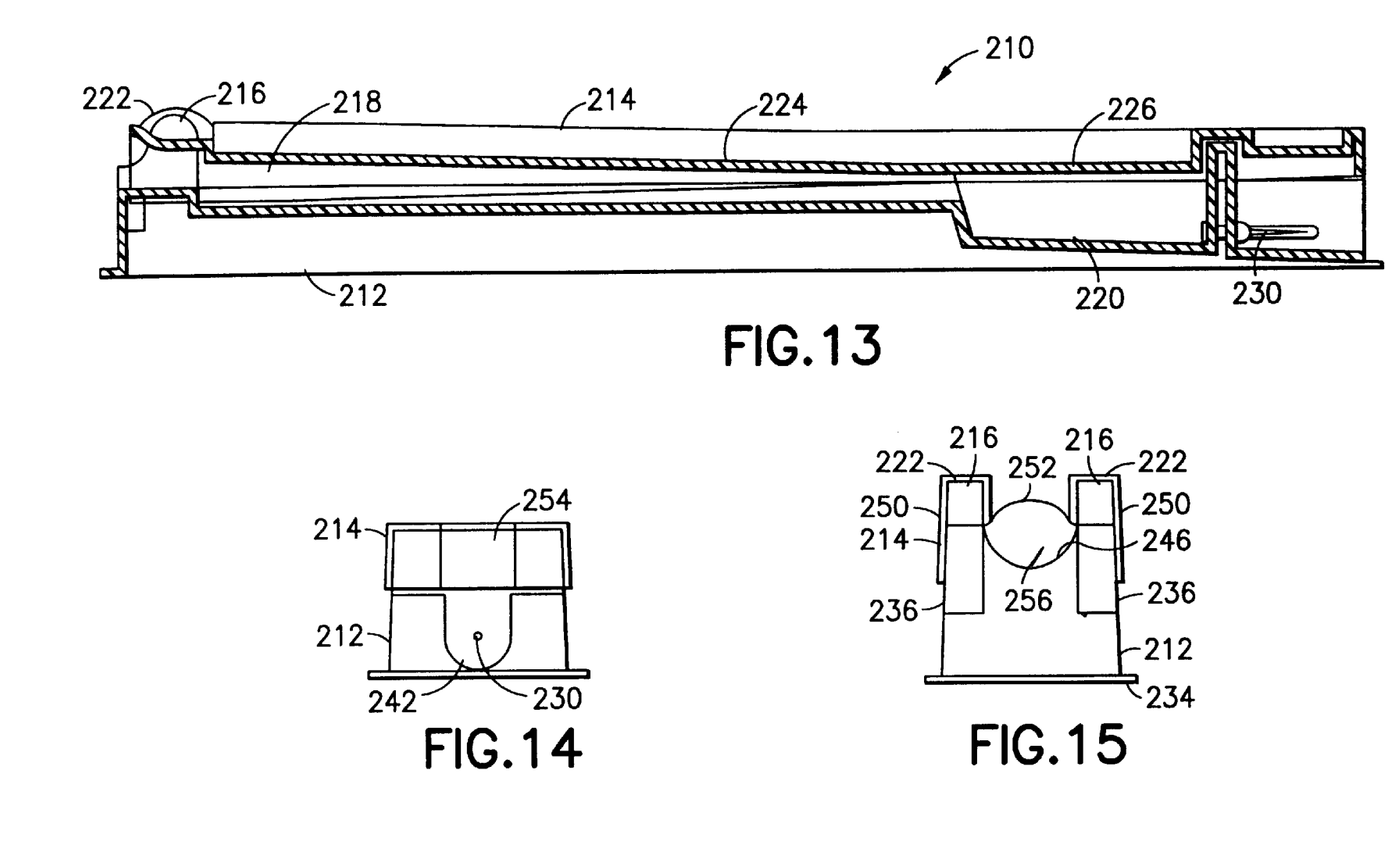
FIG. 13 is a section view of a third embodiment of the umbilical cord blood collector of the invention in a closed position.
FIG. 14 is a front end view of the third embodiment of the umbilical cord blood collector of FIG. 13 in a closed position.
FIG. 15 is a back end view of the third embodiment of the umbilical cord blood collector of FIG. 13 in a closed position.

Turning now to FIGS. 13 to 15, a third and currently preferred embodiment of the umbilical cord blood extractor 210, generally similar to the blood extractor 10 of the first embodiment, is shown. The blood extractor 210 generally includes a lower tray 212 and an upper lid 214 detached from the lower tray 212. The lower tray 212, which is described in more detail below, generally includes two preferably semicircular-shaped pivots 216, a trough 218, and a blood collection reservoir 220. The upper lid 214, which is also described in detail below, generally includes a molded recess 222 corresponding to the pivot 216 of the tray 212 and about which the upper lid 214 can be rotated on the pivot 216, a longitudinal protrusion (plunger) 224, and a reservoir cap 226.

Figure 16:
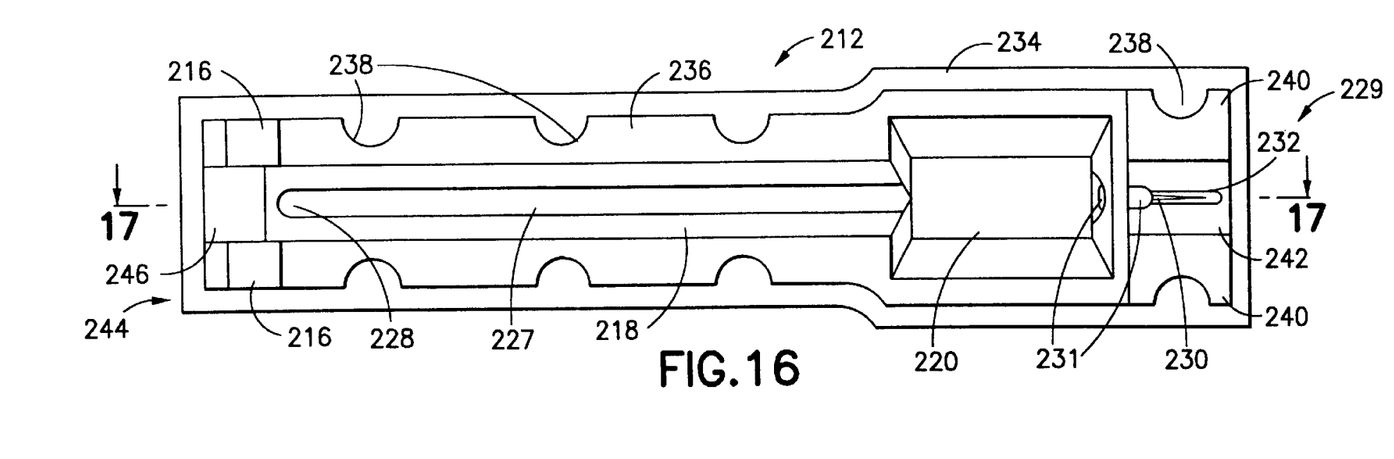
FIG. 16 is a top view of a lower tray portion of the third embodiment of the invention.
Figure 17:
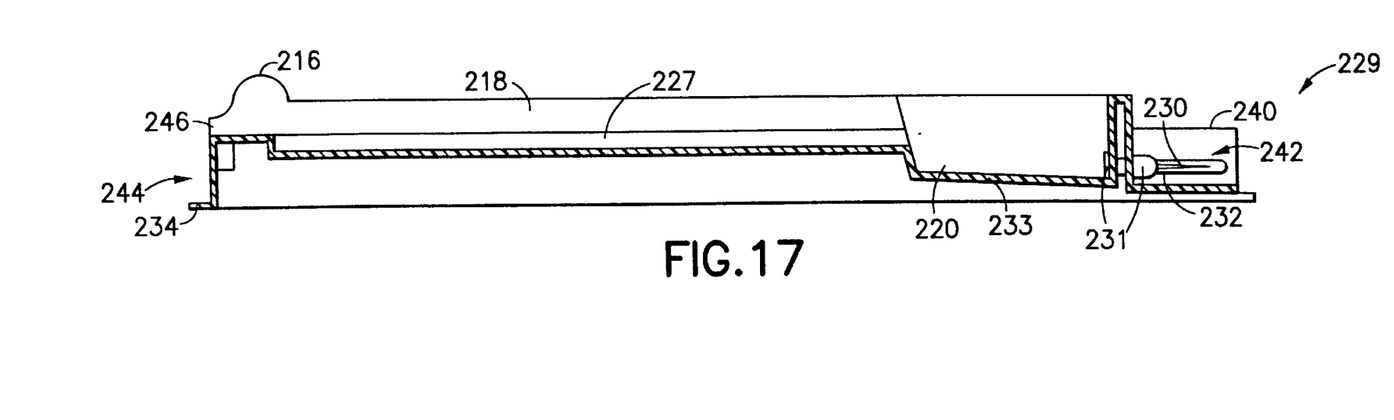
FIG. 17 is a section view through line 17—17 in FIG. 16.

More particularly, referring to FIGS. 16 and 17, the trough 218 of the lower tray 212 includes a lower portion or drain 227 which is slightly angled toward and opens into the reservoir 220 and a closed end 228 opposite the reservoir 220. In addition, the front end 229 of the lower tray 212 includes a blood collection needle 230 with a substantially rigid needle hub 231 and optionally a protective boot 232. The needle hub 231 is preferably glued to the lower tray 212 at the front end of the reservoir 220. The needle 230 is preferably an 18 to 20 gauge needle permitting maximum extraction of partially coagulated blood squeezed, as described below, from a section of umbilical cord. The floor 233 of the reservoir 220 is preferably angled toward the needle 230. In addition, the lower tray 212 includes a base 234 and lateral walls 236 extending upward from the base 234. The lateral walls 236 are preferably molded with a plurality of reinforcing indentations 238 which provide strength to the tray. At the front end 229 of the tray, a relatively shorter wall 240 is provided laterally of the needle 230 and forms a substantially semicylindrical channel (needle guide) 242 about the needle (FIGS. 14 and 16) which acts as a guide for an evacuated vial (FIG. 22) such as a VACUTAINER® available from Becton Dickenson of Franklin Lakes, N.J., and protects a user from being accidentally pricked by the needle 230. For safety, the needle 230 preferably extends to approximately one-half inch from the distal end of the needle guide 242. The back end 244 of tray 212 includes a preferably radiused umbilical cord guide 246 raised relative to the drain 227 of the trough 218 (FIGS. 15, 16, and 17).

Figure 18:
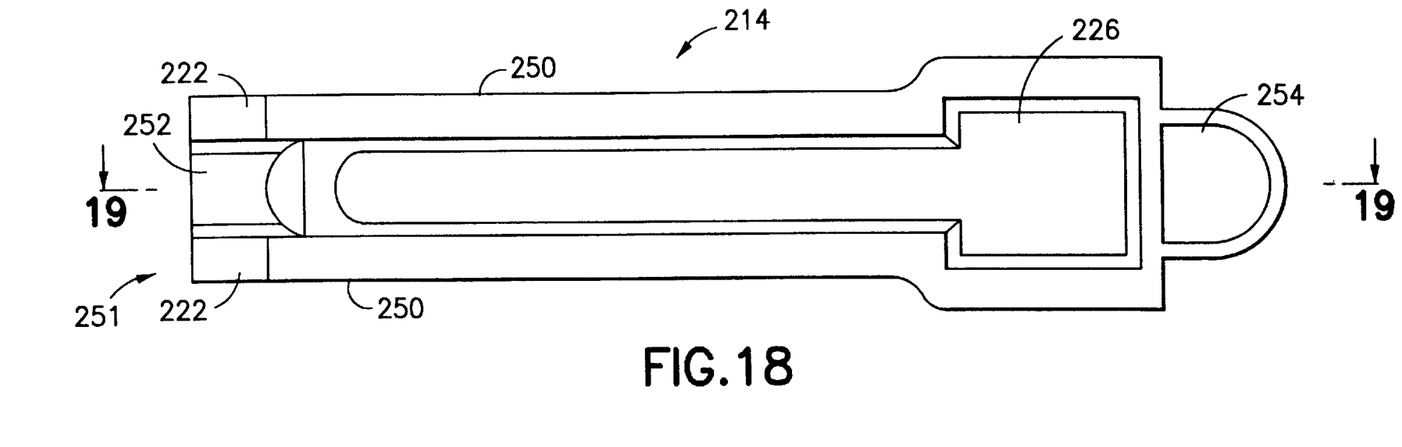
FIG. 18 is top view of an upper lid portion of the third embodiment of the invention.
Figure 19:
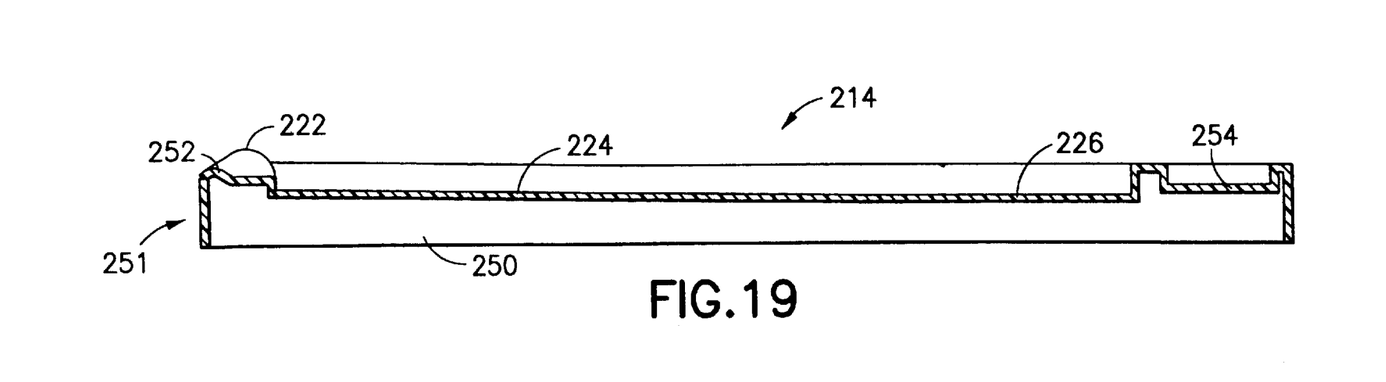
FIG. 19 is a section view through line 19—19 in FIG. 18.

Referring now to FIGS. 18 and 19, the longitudinal protrusion or plunger 224 of the upper lid 214 is preferably angled downward from the back end 251 of the lid 214 to the reservoir cap 226. The reservoir cap 226 is provided at the distal end of the plunger 224 for seating in the upper opening of the reservoir 220 of the tray 212. Descending lateral walls 250 are sized to fit around the lateral walls 236 of the tray 212 and function as blood splash guards. At the back end 251 of the lid 214, a raised contour 252 is provided. When the lid 212 is positioned on the tray 214, the raised contour 252 and the cord guide 246 together define an opening 256 at which a section of an umbilical cord can be received into the blood extractor 210 through the tray 212 and lid 214 (FIG. 15). At the front end of the lid 214 a needle shield 254 is preferably provided, which when the lid is positioned on the tray, additionally shields the needle 230 from otherwise potential accidental pricking (FIGS. 14, 18, and 19).

Figure 20:
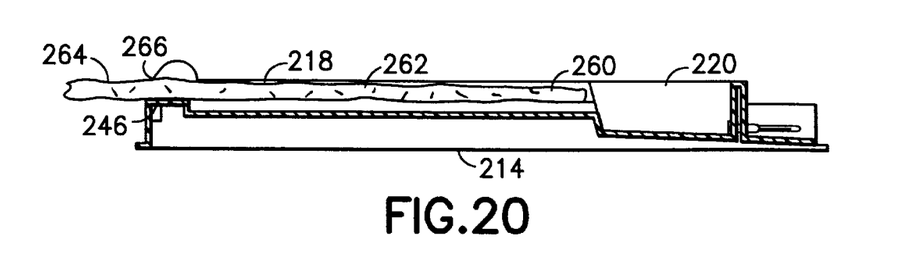
FIGS. 20–22 illustrate, in section, a method of the invention for extracting blood from a cut section of umbilical cord using the third embodiment of the umbilical cord blood extractor.

Turning now to FIG. 20, in practice, the severed end 260 of a cut section 262 of umbilical cord (regardless of whether the other end 264 of the umbilical cord is severed from or attached to the placenta) is placed into the trough 218 of the lower tray 214 with the severed end 260 directed toward the reservoir 220. If the cut section 262 is longer than the trough 218 (e.g., if the cord is still attached to the placenta), a portion 266 of the cut section 262 may extend across the cord guide 246.

Figure 21:
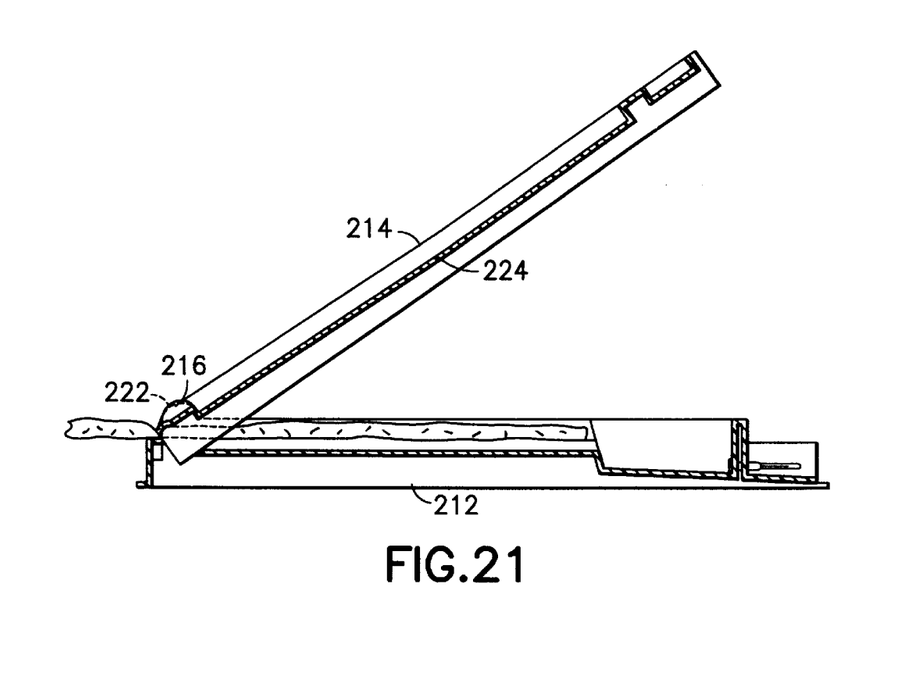
Figure 22:
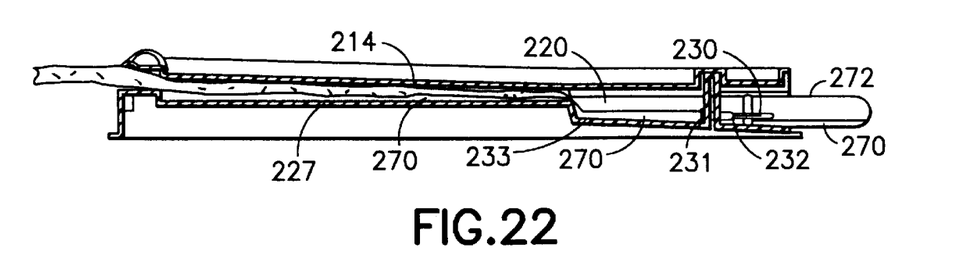

Referring to FIGS. 21 and 22, the molded recesses 222 at the back end 251 of the lid 214 are positioned over the pivots 216 (FIG. 21), and the lid 214 is then rotated about the pivots 216 until the lid is positioned substantially as shown in FIG. 22 such that the plunger 224 compresses the section of umbilical cord and squeezes blood 270 therefrom. The angle of the plunger 224 provides directional force on the section of cord to squeeze the blood 270 toward the reservoir 220. It will be appreciated that by having the lid 214 separate and detached from the tray 212 and/or by providing an opening at the end of the extractor opposite the reservoir, a large range of sizes of umbilical cords can be accommodated by the blood extractor of the invention. Referring to FIG. 22, the blood 270 drains into the drain 227, flows into the reservoir 220, and pools (due to the sloped floor 233 of the reservoir 220) about the needle hub 231. After sufficient blood is located in the reservoir 220, an evacuated vial 272 is located in the needle guide 242 and forced over the needle 230 (thereby pushing the boot 232 back to expose the needle), and blood 270 is drawn into the vial 272 from the reservoir 220.

By way of example, and not by way of any limitation, the following dimensions are provided for the umbilical cord blood extractor 210. The tray of the blood extractor has a length of approximately 10.5 inches along the base and a width of approximately 2.4 to 2.7 inches. The reservoir is approximately 1.5 inches in width, 2 inches in length, and 1.25 inches in depth. The trough has a preferably constant depth of approximately 0.5 inches and the drain within the trough has an additional depth of approximately 0.25 inches. The lateral wall height of the tray is approximately 1.5 inches between the pivot and the reservoir. The lid of the blood extractor has a length of approximately 9.3 inches, widths of approximately 1.6 inches at the portion of the lid including the trough and the molded recess, approximately 2.1 inches across the reservoir cap, and approximately 1.25 inches across the shield. The plunger, preferably along its entire length, extends downward approximately 0.5 inches from the upper surface of the lid. The blood extractor is designed for vacuum forming. In addition, the blood extractor is preferably made from a substantially clear plastic material permitting a user, such as a health care worker, to see the amount of blood extracted from the umbilical cord.

Figure 23:
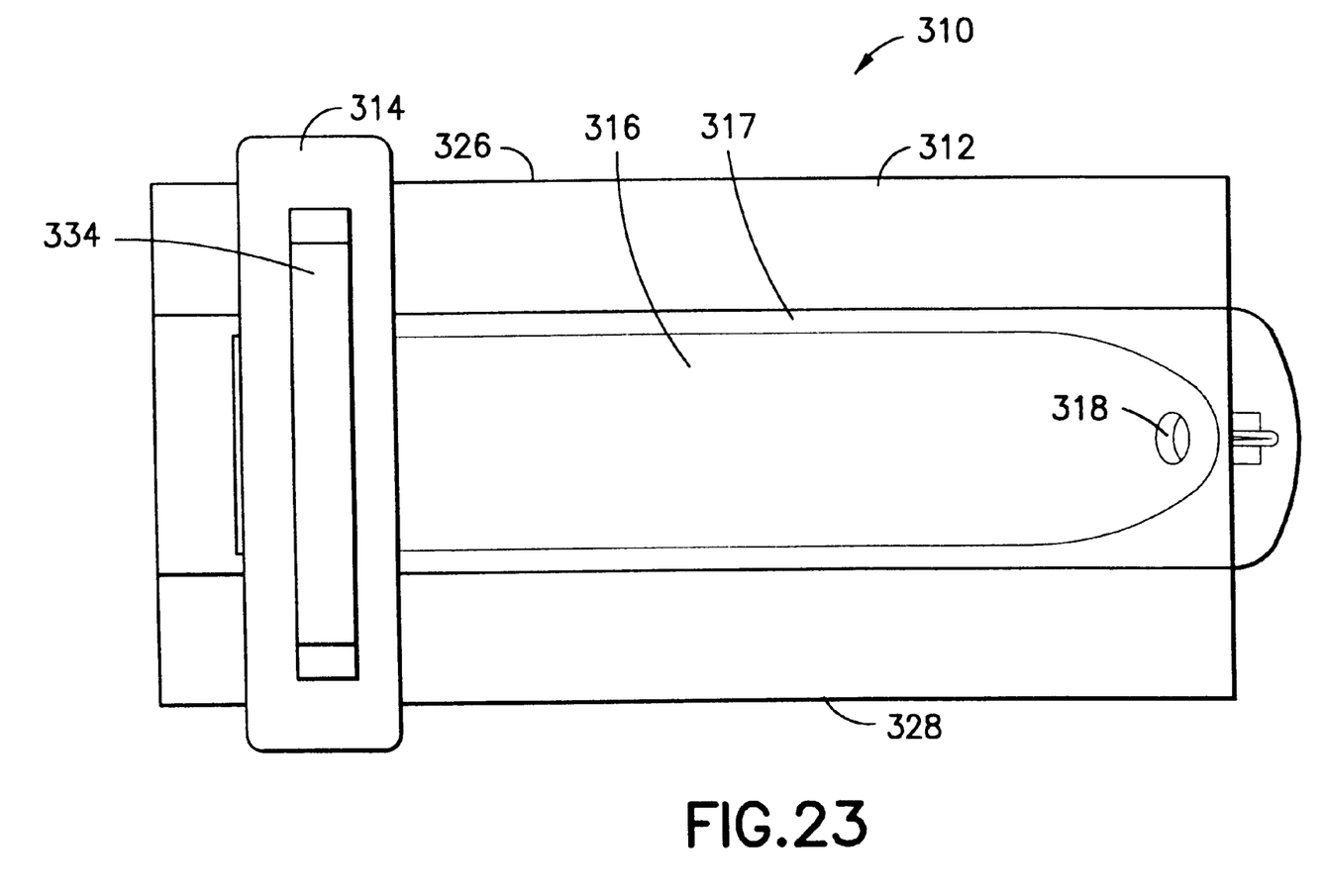
FIG. 23 is a top view of an umbilical cord blood extractor according to a fourth embodiment of the invention.
Figure 24:
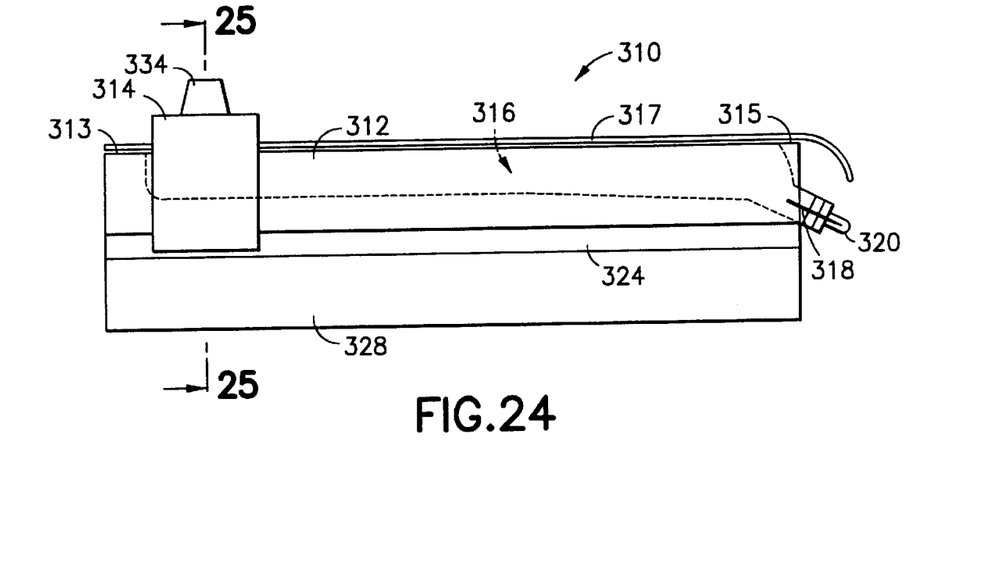
FIG. 24 is a side elevation view of the umbilical cord blood extractor of FIG. 23.
Figure 25:
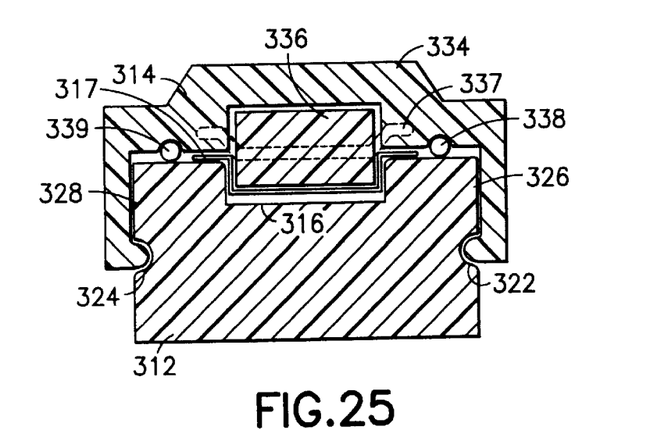
FIG. 25 is a cross-section through line 25—25 in FIG. 24.

Turning now to FIGS. 23 through 25, a fourth embodiment of an umbilical cord blood extractor 310 according to the invention is shown. The blood extractor generally includes a base member 312, a movable member 314, which is movable relative to the base member, and a splash guard 317. The base member includes a proximal end 313, a distal end 315, and a longitudinal trough 316 which is preferably set at an angle such that fluid within the trough drains toward a drain 318 at the distal end of the trough. A blood collection needle 320 with a rubber boot or sheath 322 is coupled to the drain 318 to receive blood extracted into the trough 316.

The movable member 314 is preferably coupled to the base member such that the movable member can be moved over a substantial length of the trough. Thus, as shown in FIGS. 14 and 15, the base member 314 preferably has longitudinal grooves 322, 324 along its longitudinal sides 326, 328 into which lateral arms 330, 332 of the movable member engage. The lateral arms 330, 332 of the movable member may ride in the grooves. To further assist movement of the movable member relative to the base member, rollers 338, 339 may be provided on the underside of the movable member which permit the movable member to glide across the surface of the base member. A hand grip 334 is also preferably provided on the movable member 314. The movable member includes a squeezing member 336 which extends into the trough 316. The squeezing member 336 is preferably cylindrically shaped and mounted via an axle 337 to the movable member. Thus, the squeezing member 336 is preferably rotatable about the axle, although it need not be able to rotate.

The splash guard 317 is a flexible piece of material, preferably transparent, which is sized and shaped to extend over the trough of the base member 312.

In use, the movable member is moved to the proximal end of the base member and a section of umbilical cord is placed into the trough. The splash guard is placed over the cord and between the movable member and the base member. The movable member is next moved distally, causing the squeezing member 336 to progressively squeeze the cord between the squeezing member and the surface of the trough and to extract blood from the cord section. The splash guard prevents extracted blood from splashing onto a practitioner operating the device. Blood flows from the cord section into the trough and toward the distal end of the trough where it exits through the drain (or collects at the drain if the drain is sealed until the drain is opened).

There have been described and illustrated herein several embodiments of an umbilical cord blood extractor and methods of extracting blood from an umbilical cord. While particular embodiments of the invention have been described, it is not intended that the invention be limited thereto, as it is intended that the invention be as broad in scope as the art will allow and that the specification be read likewise. Thus, while exemplar dimensions for particular features of one embodiment of the blood extractor have been disclosed, it will be appreciated that other dimensions may be used as well. Also, while particular splash resistant designs have been described with respect to certain embodiments, it will be understood other splash resistant designs can be used. In addition, while serrations are preferred in the trough and on the plunger in certain embodiments, it will be recognized that serrations need not be used. Also, while in the second embodiment, both the plunger and the trough are described as being tapered, it will be appreciated that solely one, or neither, of the trough and plunger may be tapered. Furthermore, while in certain embodiments the upper lid and lower tray have been shown to be coupled by a hinge, it will be appreciated that the upper lid and lower tray do not have to be coupled by a hinge. Moreover, while in the third embodiment, a movable member has been shown to include a squeezing member which is coupled to the movable member, it will be appreciated that the squeezing member and the movable member may be of a unitary construction, or may be of a shape other than cylindrical. In addition, the movable member may be otherwise coupled to the base member than as shown. For example, the pivots and molded recesses may be provided to the upper (movable) member and lower (base) member, respectively. It will therefore be appreciated by those skilled in the art that yet other modifications could be made to the provided invention without deviating from its spirit and scope as so claimed.

We claim:

1. An umbilical cord blood extractor for extracting blood from a section of umbilical cord, said blood extractor comprising:
    a) a lower member having a longitudinal trough which receives the cut section of umbilical cord and having a reservoir provided at an end of said trough; and
    b) an upper member having a protrusion sized and shaped to be at least partially received in said trough,
        one of said upper member and said lower member including a pivot at which the other of said upper member and said lower member can rotate relative to said one of said upper member and said lower member,
        wherein when said upper member is closed on said lower member, the cut section of the umbilical cord is squeezed between said protrusion and said trough such that blood is extracted out of the umbilical cord.

2. An umbilical cord blood extractor according to claim 1, wherein:
    said trough has a drain which opens into said reservoir.

3. An umbilical cord blood extractor for extracting blood from a section of umbilical cord, said blood extractor comprising:
    a) a lower member having a longitudinal trough which receives the cut section of umbilical cord, said longitudinal trough having a first squeezing surface having a first longitudinal axis; and
    b) an upper member having a protrusion sized and shaped to be at least partially received in said trough, said protrusion having a second squeezing surface having a second longitudinal axis,
        one of said upper member and said lower member including a pivot at which the other of said upper member and said lower member can rotate relative to said one of said upper member and said lower member,
        wherein when said upper member is closed on said lower member, the cut section of the umbilical cord is squeezed between said protrusion and said trough such that blood is extracted out of the umbilical cord, and wherein
        when said upper member is in a fully closed position relative to said lower member, said second longitudinal axis of said second squeezing surface of said protrusion is angled relative to said first longitudinal axis of said first squeezing surface of said trough.

4. An umbilical cord blood extractor for extracting blood from a section of umbilical cord, said blood extractor comprising:
    a) a lower member having a longitudinal trough which receives the cut section of umbilical cord; and
    b) an upper member having a protrusion sized and shaped to be at least partially received in said trough,
        one of said upper member and said lower member including a pivot at which the other of said upper member and said lower member can rotate relative to said one of said upper member and said lower member,
        wherein when said upper member is closed on said lower member, the cut section of the umbilical cord is squeezed between said protrusion and said trough such that blood is extracted out of the umbilical cord, and wherein
        said upper member and said lower member each have a back end, and said back end of at least one of said upper member and said lower member defines an opening through which the section of umbilical cord can be received.

5. An umbilical cord blood extractor according to claim 1, further comprising:
c) a needle coupled to said lower member such that said needle is adapted to permit fluid to flow from said reservoir through said needle.

6. An umbilical cord blood extractor according to claim 5, wherein:
said needle is an 18–20 gauge needle.

7. An umbilical cord blood extractor according to claim 5, wherein:
said reservoir includes a floor surface which is sloped toward said needle.

8. An umbilical cord blood collector according to claim 5, wherein:
at least one of said upper member and said lower member defines a guide for locating an evacuated vial over said needle.

9. An umbilical cord blood extractor according to claim 1, wherein:
at least one of said upper member and said lower member is provided with guide means for guiding an evacuated vial to a location adjacent said reservoir.

10. An umbilical cord blood extractor for extracting blood from a section of umbilical cord, said blood extractor comprising:
a) a lower member having a longitudinal trough which receives the cut section of umbilical cord; and
b) an upper member having a protrusion sized and shaped to be at least partially received in said trough,
one of said upper member and said lower member including a pivot at which the other of said upper member and said lower member can rotate relative to said one of said upper member and said lower member,
wherein when said upper member is closed on said lower member, the cut section of the umbilical cord is squeezed between said protrusion and said trough such that blood is extracted out of the umbilical cord, and wherein
said lower member has a base portion and lateral walls on either side of said trough, said lateral walls being provided with a plurality of reinforcing indentations.

11. An umbilical cord blood extractor according to claim 1, wherein:
at least one of said upper member and said lower member is made from a substantially clear material.

12. An umbilical cord blood extractor for extracting blood from a section of umbilical cord and providing the blood to an evacuated vial, said blood extractor comprising:
a) a lower member having a longitudinal trough which receives the cut section of umbilical cord and a reservoir at an end of said trough; and
b) an upper member having a protrusion sized and shaped to be at least partially received in said trough,
at least one of said upper member and said lower member being provided with guide means for guiding the evacuated vial to a location adjacent said reservoir,
wherein when said upper member is closed on said lower member, the cut section of the umbilical cord is squeezed between said protrusion and said trough such that blood is extracted out of the umbilical cord.

13. An umbilical cord blood extractor according to claim 12, wherein:
said trough has a drain which opens into said reservoir.

14. An umbilical cord blood extractor according to claim 12, wherein:
said longitudinal trough has a first squeezing surface having a first longitudinal axis, and said protrusion has a second squeezing surface having a second longitudinal axis, and
when said upper member is in a fully closed position relative to said lower member, said second longitudinal axis of said second squeezing surface of said protrusion is angled relative to said first longitudinal axis of said first squeezing surface of said trough.

15. An umbilical cord blood extractor according to claim 12, wherein:
said upper member and said lower member each have a back end, and said back end of at least one of said upper member and said lower member defines an opening through which the section of umbilical cord can be received.

16. An umbilical cord blood extractor according to claim 12, further comprising:
c) a needle coupled to said reservoir and extending into said guide means such that said needle is adapted to permit fluid to flow from said reservoir through said needle and into the evacuated vial.

17. An umbilical cord blood extractor according to claim 16, wherein:
said needle is an 18–20 gauge needle.

18. An umbilical cord blood extractor according to claim 16, wherein:
said guide means shields said needle.

19. An umbilical cord blood extractor according to claim 16, wherein:
said reservoir includes a floor surface which is sloped toward said needle.

20. An umbilical cord blood collector according to claim 12, wherein:
a first of said upper member and said lower member includes a pivot portion at which a second of said upper member and said lower member can rotate relative to said first of said upper member and said lower member.

21. A method of extracting blood from a section of umbilical cord, said method comprising:
a) placing a section of umbilical cord in a tray having a surface and a pivot;
b) rotating a cover about the pivot of the tray to squeeze the section of umbilical cord between the cover and the tray to thereby extract the blood from the section of umbilical cord onto the tray; and
c) collecting the blood.

* * * * *